United States Patent

Tomura et al.

Patent Number: 6,027,719
Date of Patent: Feb. 22, 2000

[54] AQUEOUS COSMETIC COMPOSITION CONTAINING STABLY SOLUBILIZED URIC ACID AND WATER-SOLUBLE POLYMER AND METHOD FOR STABLY SOLUBILIZING URIC ACID IN AQUEOUS COSMETIC COMPOSITION

[75] Inventors: Kazuyo Tomura; Akiko Ogata; Kakunori Mikami; Yoshio Tsujino, all of Osaka, Japan

[73] Assignee: Yamahatsu Sangyo Kaisha, Ltd., Osaka-fu, Japan

[21] Appl. No.: 08/887,932

[22] Filed: Jul. 3, 1997

[30] Foreign Application Priority Data

Apr. 28, 1997 [JP] Japan .................. 9-110932

[51] Int. Cl.⁷ .................................. A61K 7/48
[52] U.S. Cl. ............................... 424/78.02
[58] Field of Search ............. 424/78.16, 78.02

[56] References Cited

FOREIGN PATENT DOCUMENTS

| | | |
|---|---|---|
| 07 16846 A1 | 6/1996 | European Pat. Off. . |
| 61 118312 | 6/1986 | Japan . |
| 61 183204 | 8/1986 | Japan . |
| 01 275511 | 11/1989 | Japan . |
| 01 275516 | 11/1989 | Japan . |

OTHER PUBLICATIONS

Abstract of JP–51–048441 Nagai et al.

Abstract of JP–01197813 Takagishi et al.

*Primary Examiner*—Peter F. Kulkosky
*Attorney, Agent, or Firm*—Birch, Stewart Kolasch & Birch, LLP

[57] ABSTRACT

An aqueous cosmetic composition containing uric acid in a stably solubilized state together with an acrylic polymer is disclosed. The composition is adjusted to pH equal to or higher than $pK_1$ of uric acid, in particular, pH 7 or higher by an alkali to solubilize uric acid. A method for stably solubilizing uric acid in an aqueous cosmetic composition is also disclosed.

16 Claims, 1 Drawing Sheet

AQUEOUS COSMETIC COMPOSITION CONTAINING STABLY SOLUBILIZED URIC ACID AND WATER-SOLUBLE POLYMER AND METHOD FOR STABLY SOLUBILIZING URIC ACID IN AQUEOUS COSMETIC COMPOSITION

FIELD OF THE INVENTION

The present invention relates to an aqueous cosmetic composition containing stably solubilized uric acid together with a water-soluble polymer, especially, an acrylic polymer, and a method for stably solubilizing uric acid in an aqueous cosmetic composition.

BACKGROUND OF THE INVENTION

Uric acid as well as its salt and derivative (hereinafter they are simply referred to as "uric acid" altogether) are used in various cosmetic compositions as a substrate of one of oxidases, uricase, a stabilizer of a moisturizer, an ingredient for preventing skin roughness, an antidandruff ingredient and the like. For example, JP 61-118312 A discloses a keratin fiber dyeing composition of pH 4 to 10.5 which comprises uric acid, an ampholytic surfactant, a thickener and the like and a method for dyeing keratin fiber using the composition. JP 61-183204 A discloses a cosmetic composition comprising a moisturizer and uric acid as a stabilizer for the moisturizer. JP 63-246313 A (U.S. Pat. No. 4,961,925) discloses a hair cosmetic composition of pH 7.5 to 8.5 which comprises dielectron reducing oxidase, uric acid as a donor of the enzyme and the like. JP 1-275511 A discloses a topical composition for skin external use containing uric acid for preventing skin roughness. JP 1-275516 A discloses an antidandruff composition containing uric acid. JP 8-217652 (EP 0716846 A) discloses an oxidation hair dyeing composition of pH 6.7 to 9.5 which comprises uric acid, potassium hydroxide and/or monoethanolamine and the like.

On the other hand, since the water-solubility of uric acid is very low such as about 0.0067%, at present, only a small amount of uric acid can be used in case of an aqueous solubilized system. In addition, in case of a dispersion system wherein uric acid is added in excess of its solubility, there are many problems such as precipitation of uric acid, limitation of containers to be used for packaging end products due to clogging of orifices thereof and the like.

Moreover, although uric acid can be solubilized in water to a certain extent by appropriately choosing an alkali, mere solubilization is insufficient for practical use due to such problems as drip and less fitness for hair or skin upon application, and the like. Then, in practice, it is necessary to add surfactants and polymers in view of usability.

However, in aqueous cosmetic compositions containing surfactants and polymers, no satisfactory technique for stably solubilizing uric acid has yet been found.

OBJECTS OF THE INVENTION

One object of the present invention is to provide a technique for stably solubilizing uric acid in an aqueous cosmetic composition containing uric acid and a water-soluble polymer.

This object as well as other objects and advantages of the present invention will become apparent to those skilled in the art from the following description with making reference to the accompanying drawing.

SUMMARY OF THE INVENTION

Figure 1:
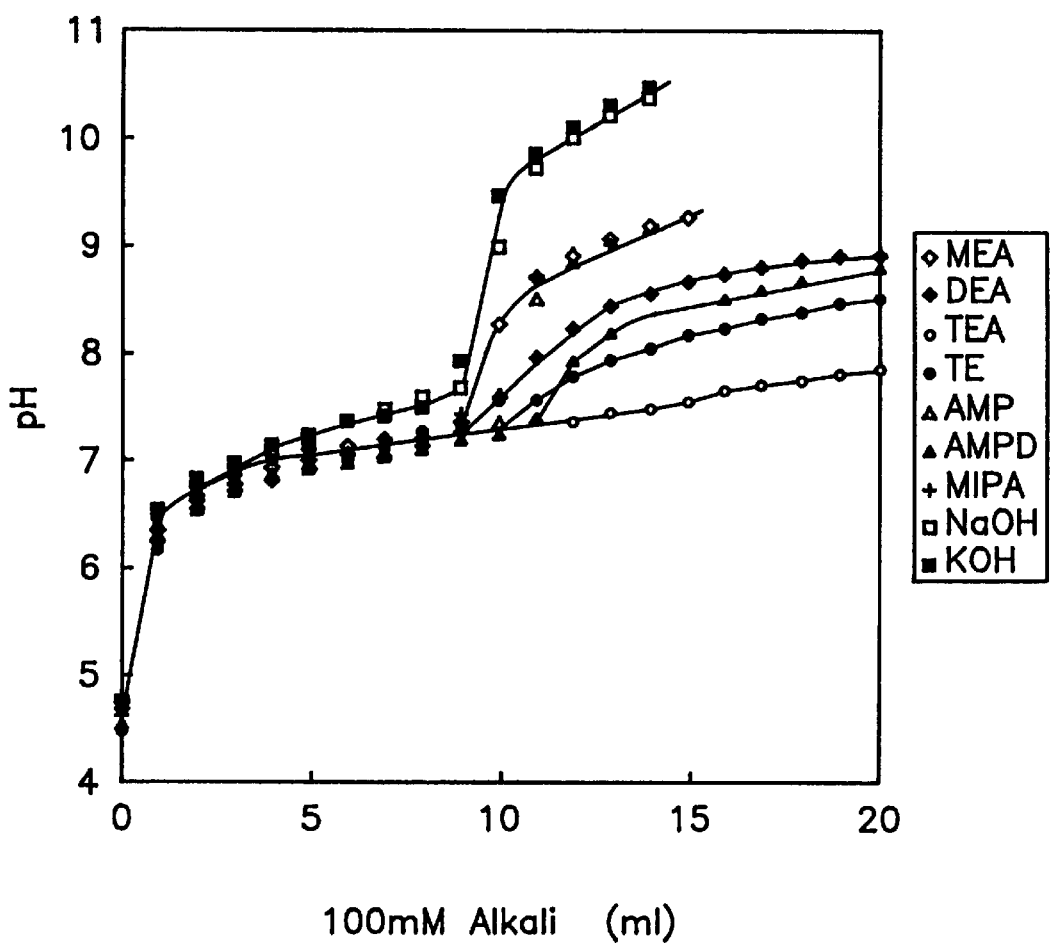
FIG. 1 illustrates titration curves of a uric acid solution in water with various alkalis.

The present inventors have intensively studied behavior of uric acid in an aqueous cosmetic composition. As a result, it has been found that uric acid can be stably solubilized in such a composition by combining a specific polymer and an alkali and adjust pH of the composition to a specific range.

That is, in one aspect, the present invention provides an aqueous cosmetic composition containing uric acid in a stably solubilized state which comprises uric acid, an acrylic polymer, an alkali and water, said composition being adjusted to pH equal to or higher than $pK_1$ of uric acid, in particular, pH 7 or higher by the alkali to solubilize uric acid.

In another aspect, the present invention provides a method for stably solubilizing uric acid in an aqueous cosmetic composition which comprises adjusting pH of the composition equal to or higher than $pK_1$ of uric acid, in particular, pH 7 or higher by an alkali to solubilize uric acid.

In the present invention, preferred examples of the acrylic polymer include carboxyvinyl polymers, copolymers of acrylic and methacrylic acid polymers and alkyls, or copolymers of acrylic and methacrylic acid polymers and polyoxyethylene glycol ether of higher alcohols. Preferred examples of the alkali include amines.

According to the present invention, a relatively large amount of uric acid such as 0.01 to 2.0% by weight can be stably solubilized to provide an aqueous cosmetic composition, for example, hair dyeing composition which exhibits excellent activity of uric acid and sufficient effect of the water-soluble polymer.

DETAILED DESCRIPTION OF THE INVENTION

The terms "stably solubilizing" and "stably solubilized state" used herein mean that uric acid is maintained in a solubilized state without separation in a cosmetic composition.

The term "acrylic and methacrylic polymer" includes homopolymers and copolymers of acrylic acid, acrylates, methacrylic acid and/or methacrylates.

Examples of uric acid to be used in the present invention includes, in addition to uric acid itself, inorganic salts of uric acid such as sodium urate, potassium urate, calcium urate, sodium hydrogen urate, potassium hydrogen urate, calcium hydrogen urate, etc.; organic salts of uric acid such as ammonium urate, ammonium hydrogen urate, salts of uric acid with various amino acids, etc.; and various uric acid derivatives such as alkyl modified uric acids (e.g., 3-N-methyl uric acid, 3-N-lauryl uric acid, 7-N-butyl uric acid, 1-N-ethyl uric acid, 9-N-lauryl uric acid, 3,7-N-dimethyl uric acid, etc.), uric acid glycosides (e.g., 3-N-ribosyl uric acid, 9-N-glycosyl uric acid, etc.) and the like.

These uric acid, salts and derivatives can be used alone or in combination and can be used in an amount of, as uric acid itself, 0.01 to 2% by weight, preferably 0.1 to 1.3% by weight based on the total weight of the cosmetic composition. When the amount of uric acid is lower than 0.01% by weight, its activity is insufficient. On the other hand, when the amount of uric acid is more than 2% by weight, stable solubilization thereof is hardly expected.

The acrylic polymer to be used in the present invention is not specifically limited and any polymer normally used in cosmetic compositions can be used. Examples thereof include carboxyvinyl polymers mainly composed of acrylic acid; acrylic and methacrylic acid-alkyl copolymers such as copolymers of acrylic and methacrylic acid polymers and alkyls; acrylic and methacrylic acid polyoxyethylene glycol ether copolymers such as copolymers of acrylic and methacrylic acid polymers and polyoxyethylene glycol ethers of higher alcohols (e.g., higher alcohols having 12 to 32 carbon atoms) and the like. Preferably, carboxyvinyl polymers, Aculyn™ 22 (copolymer of acrylic and methacrylic acid polymer and polyoxyethylene glycol ether of stearyl alcohol manufactured and sold by Rhoma and Haas Company), Carbopol (acrylic and methacrylic-alkyl copolymer manufactured and sold by B.F. Goodrich Co.) and the like can be used. The acrylic polymer can be used alone or in combination in an amount suitable for providing the desired properties to the aqueous cosmetic composition, normally, 0.01 to 10.0% by weight, preferably, 0.1 to 5% by weight based on the total weight of the composition, though the amount of the acrylic polymer is not specifically limited.

Examples of the alkali to be used in the present invention include amines such as monoethanolamine (MEA), diethanolamine (DEA), triethanolamine (TEA), 2-amino-2-methyl- 1-propanol (AMP), 2-amino-2-methyl-1,3-propanediol (AMPD), monoisopropanolamine (MIPA), tetrakis(2-hydroxyisopropyl)ethylenediamine (TE) and the like. These alkalis can be used alone or in combination and it is possible to use ammonia and inorganic alkalis such as sodium hydroxide, potassium hydroxide and the like. Although the amount of the alkali to be added to the composition is not specifically limited, the amount should be sufficient for adjusting pH of the composition equal to or higher than $pK_1$ of uric acid, preferably, pH 7 or higher. Thereby, uric acid can be stably solubilized in an aqueous cosmetic composition.

Especially, in the present invention, it is preferred to use an amine as the alkali together with the acrylic polymer because uric acid can be solubilized very stably.

According to the present invention, uric acid is added to a major portion of water to be used for the production of the aqueous cosmetic composition and pH of the resultant mixture is adjusted to the desired pH, followed by addition of the acrylic polymer and, if necessary, warming to dissolve the polymer. Then, other ingredients are added to obtain the desired aqueous cosmetic composition in various preparation forms such as gel, paste, cream and the like. Thus, an aqueous cosmetic composition for application to hair, skin, nails, oral cavity or the like, which contains stably solubilized uric acid together with the acrylic polymer can be obtained.

In the present invention, according to the desired preparation form, surfactants such as anionic surfactants, cationic surfactants, nonionic surfactants, etc.; oily agents such as higher alcohols, higher fatty acids, paraffin wax, hydrocarbon oils, ester oils, silicone oils, etc.; hair dyes such as oxidation dyes, direct dyes, etc.; moisturizers such as glycerin, propylene glycol, etc.; thickeners; preservatives; anti-oxidants; UV absorbers; metal chelating agents; enzymes such as uricase; various pharmacologically active ingredients; perfumes; and the like can be appropriately added in so far as they do not adversely affect the present invention.

The following tests and examples further illustrate the present invention in detail but are not to be construed to limit the scope of the present invention. In the tests and examples, all the "percents (%)" are by weight unless otherwise stated.

Test 1

Effect of various alkalis on solubilization of uric acid

In literature, it is said that uric acid has $pK_1$ of 5.8 and $pK_2$ of 10.3.

Then, pH titration of uric acid solutions in water was carried out by using various alkalis under the following conditions to prepare pH curves and observe the state of uric acid in the respective solutions.

The results are shown in Table 1 and FIG. 1.

Conditions: An each alkali solution (100 mM) was added to 100 ml of 10 mM uric acid solution in water (20±1° C.).

Apparatus: pH meter manufactured by HORIBA

TABLE 1

| Alkali | pH | State of uric acid |
|---|---|---|
| MEA | 9.08 | dissolved |
| DEA | 8.02 | dissolved |
| TEA | 7.74 | dissolved |
| AMP | 8.87 | dissolved |
| AMPD | 8.42 | dissolved |
| MIPA | 8.96 | dissolved |
| TE | 8.47 | dissolved |
| NaOH | 10.00 | dissolved |
| KOH | 10.14 | dissolved |

As can be seen from FIG. 1 and Table 1, it has been found that uric acid is completely dissolved at a pH range equal to or above its $pK_1$ in the presence of various alkalis to form uniform solubilized systems. Although uric acid can be dissolved by sodium hydroxide or potassium hydroxide, a high pH such as 10 or higher is required to dissolve a large amount of uric acid (0.8% or higher), which is undesirable for a cosmetic composition to be applied to a human being from the viewpoint of irritation.

Test 2

Effect of combinations of various alkalis and water-soluble polymers on stability of solubilized uric acid in water Various alkalis were added to 1% solutions of uric acid in water to completely dissolve uric acid. Then, various water-soluble polymers were mixed with the above uric acid solutions, respectively, in the final concentration of 2% to prepare sample solutions (in case of Carbopol ETD2020, the final concentration of the polymer was 1%). The sample solutions were subjected to repetition of a cycle of storage at 5° C. for 12 hours and then incubation at 43° C. for 12 hours for 5 days to evaluate whether or not the solubilized uric acid separated out by mixing with the water-soluble polymers according to the following criteria.

A: solubilization of uric acid

B: separating out of very fine crystals of uric acid

C: separating out of uric acid

The results are shown in Table 2.

TABLE 2

|  | Water (control) | Polymer* | | | | | |
|---|---|---|---|---|---|---|---|
|  |  | HEC | xanthan gum | CMC | Aculyn 22 | Carbopol ETD2020 | Carbopol 981 |
| MEA | C | B | C | C | A | C | C |
| DEA | C | B | C | C | A | C | C |
| TEA | C | B | C | C | A | A | C |
| AMP | C | B | C | C | A | A | A |
| AMPD | C | B | C | C | A | A | A |
| MIPA | C | C | C | C | A | A | A |
| TE | A | C | C | C | A | C | C |
| KOH | C | A | B | C | C | C | C |
| NaOH | A | A | A | C | A | C | C |

*: Water-soluble polymers
HEC: hydroxyethyl cellulose
CMC: carboxymethyl cellulose
Aculyn 22: copolymer of acrylic and methacrylic acid polymer and polyoxyethylene glycol ether of higher alcohol (30% aqueous solution) [Acrylates/Steareth-20 Methacrylate Copolymer (CTFA ADOPTED NAME)]
Carbopol ETD2020: acrylic and methacrylic acid polymer-alkyl copolymer [Acrylates/C10–30 Alkyl Acrylate Crosspolymer]
Carbopol 981: carboxyvinyl polymer As can be seen from Table 2, especially, when Aculyn 22 and other acrylic polymers were used, stable solubilization of uric acid was achieved.

Test 3

Effect of concentration of acrylic polymer on stability of solubilized uric acid Aculyn 22 was added to aqueous uric acid solutions containing different concentrations of uric acid dissolved with diethenolamine and the resultant mixtures were subjected to repetition of the above cycle for 5 days to evaluate the state of uric acid according to the same criteria.

The results are shown in Table 3.

TABLE 3

| Uric acid | Aculyn 22 (%) | | | | |
|---|---|---|---|---|---|
| (%) | 0 | 0.2 | 1.0 | 1.5 | 2.0 |
| 0.4 | C | A | A | A | A |
| 0.6 | C | B | A | A | A |
| 0.8 | C | C | A | A | A |
| 1.0 | C | C | C | C | A |

A: solubilization of uric acid
B: separating out of very fine crystals of uric acid
C: separating out of uric acid As can be seen from Table 3, as the concentration of Aculyn 22 is increased, a larger amount of uric acid can be stably solubilized.

Test 4

Effect of various alkalis and Aculyn 22 on stability of solubilized uric acid

In order to investigate ability of various alkalis to solubilize uric acid in the presence of Aculyn 22, 0.5% or 1.0% of uric acid was added to water and then various alkalis were added thereto, respectively, until complete solubilization of uric acid was achieved. After addition of alkalis, Aculyn 22 was added to the respective solutions in an amount of 3% and the mixtures were subject to repetition of the above cycle for 15 days. As a control, the uric acid solutions without addition of Aculyn 22 (0%) were also subjected to repetition of the above cycle. Five days and 15 days after initiation of this test, the state of uric acid was evaluated according to the same criteria. The results are shown in Table 4.

TABLE 4

| Alkali | Aculyn 22 (%) | Uric acid (%) | Initial | 5 days | 15 days |
|---|---|---|---|---|---|
| MEA | 3.0 | 0.5 | A | A | A |
|  |  | 1.0 | A | A | A |
|  | 0 | 0.5 | A | C | C |
|  |  | 1.0 | A | C | C |
| DEA | 3.0 | 0.5 | A | A | A |
|  |  | 1.0 | A | A | A |
|  | 0 | 0.5 | A | C | C |
|  |  | 1.0 | A | C | C |
| TEA | 3.0 | 0.5 | A | A | A |
|  |  | 1.0 | A | A | A |
|  | 0 | 0.5 | A | C | C |
|  |  | 1.0 | A | C | C |
| AMP | 3.0 | 0.5 | A | A | A |
|  |  | 1.0 | A | A | A |
|  | 0 | 0.5 | A | C | C |
|  |  | 1.0 | A | C | C |
| AMPD | 3.0 | 0.5 | A | A | A |
|  |  | 1.0 | A | A | A |
|  | 0 | 0.5 | A | C | C |
|  |  | 1.0 | A | C | C |
| MIPA | 3.0 | 0.5 | A | A | A |
|  |  | 1.0 | A | A | A |

TABLE 4-continued

| Alkali | Aculyn 22 (%) | Uric acid (%) | Initial | 5 days | 15 days |
|---|---|---|---|---|---|
|  | 0 | 0.5 | A | C | C |
|  |  | 1.0 | A | C | C |
| TE | 3.0 | 0.5 | A | A | A |
|  |  | 1.0 | A | A | A |
|  | 0 | 0.5 | A | A | A |
|  |  | 1.0 | A | A | C |

A: solubilization of uric acid
B: separating out of very fine crystals of uric acid
C: separating out of uric acid As can be seen from Table 4, when 3% of Aculyn 22 was added, uric acid was stably solubilized even 15 days after initiation of the test with any alkali used.

EXAMPLE 1

| One-package hair dye (gel) | |
|---|---|
| Ingredient | Amount (%) |
| p-Phenylenediamine | 1.5 |
| m-Phenylienediamine hydrochloride | 0.12 |
| p-Aminophenol | 0.6 |
| m-Aminophenol | 0.08 |
| N-acetyl-1-cysteine | 0.08 |
| Aculyn 22 | 2.5 |
| Glycerin | 2.0 |
| Polyoxyethylene methylglycoside | 1.0 |
| Polypeptide coconut oil fatty acid potassium salt | 1.0 |
| Diethanolamine | 0.5 |
| Monoethanolamine | pH 9.2 balance |
| Uric acid | 1.0 |
| Uricase (20 ku/g) | 1.0 |
| Purified water | balance |
| Total | 100.0 |

According to this formulation, uric acid was added to a part of water to be used and the mixture was adjusted to pH 9.2 with monoethanol amine. Then, the remaining ingredients were added thereto to obtain the desired hair dye preparation.

This preparation was coated on a white hair, which was treated at 30° C. for 30 minutes, washed with water, shampooed and then dried. The white hair was dyed in grayish color.

EXAMPLE 2

| Sunscreen milky lotion | |
|---|---|
| Ingredient | Amount (%) |
| Uric acid | 0.1 |
| Triethanolamine | pH 7.8 balance |
| Aculyn 22 | 0.3 |
| Glycerin | 1.0 |
| Polyoxyethylene (5) alkyl ether | 1.0 |
| Decaglycerol monoleate | 0.5 |
| Cetanol | 0.2 |
| Purified water | balance |
| Total | 100.0 |

Uric acid was added to water and the mixture was adjusted to pH 7.8 with triethanolamine. Then, the remaining ingredients were added thereto. The mixture was adjusted to pH 7.8 with triethanolamine again to obtain the desired sunscreen milky lotion.

EXAMPLE 3

Hand cream

| Ingredient | Amount (%) |
| --- | --- |
| Uric acid | 0.2 |
| Diethanolamine | pH 8.2 balance |
| Stearic acid | 14.0 |
| Aculyn 22 | 0.6 |
| Vaseline | 1.5 |
| Self-emulsifiable glycerol monostearate | 2.5 |
| Polyoxyethylene (20) sorbitan monostearate | 1.5 |
| Propylene glycol | 4.0 |
| Perfume | 0.05 |
| Methylparaben | 0.05 |
| Purified water | balance |
| Total | 100.0 |

Uric acid was added to water and dissolved with diethanolamine. The remaining ingredients except the perfume were added thereto and, if necessary, the mixture was warmed to dissolve the ingredients. After cooling, the perfume was added and pH was adjusted to 8.2 with diethanolamine to obtain the desired hand cream.

EXAMPLE 4

One-package hair dye

| Ingredient | Amount (%) |
| --- | --- |
| p-Phenylenediamine | 0.8 |
| p-Aminophenol | 0.2 |
| 1-Cysteine | 0.1 |
| Aculyn 22 | 2.0 |
| Polyoxyethylene (50) hydrogenated castor oil | 1.0 |
| Uric acid | 0.5 |
| Tetrakis (2-hydroxyisopropyl) ethylenediamine | pH 8.5 balance |
| Enzyme (20 ku/g) | 1.0 |
| Purified water | balance |
| Total | 100.0 |

Uric acid and Aculyn 22 were added to water and the mixture was adjusted to pH 8.5 with tetrakis(2-hydroxyisopropyl)ethylenediamine. Then, the remaining ingredients were added thereto to obtain the desired hair dye preparation.

This preparation was coated on a white hair, which was treated at 30° C. for 30 minutes, washed with water, shampooed and then dried. The white hair was dyed in brownish color.

As described hereinabove, according to the present invention, an aqueous cosmetic composition containing stably solubilized uric acid together with a water-soluble polymer can be obtained.

What is claimed is:

1. An aqueous cosmetic composition which consists essentially of from 0.01 to 2.0% by weight of uric acid, an acrylic polymer, wherein said acrylic polymer is a carboxyvinyl polymer mainly comprised of acrylic acid, an acrylic and methacrylic acid-alkyl copolymer, or a copolymer composed of an acrylic and methacrylic acid and a polyoxyethylene glycol ether of a higher alcohol in an amount of about 0.01 to 10% by weight, an alkali and water, wherein said composition is adjusted to a pH equal to or higher than $pK_1$ of uric acid with the alkali, wherein the uric acid is solubilized.

2. An aqueous cosmetic composition which consists essentially of:
   from 0.01 to 2.0% by weight of uric acid;
   an acrylic polymer, wherein said acrylic polymer is a carboxyvinyl polymer mainly comprised of acrylic acid, an acrylic and methacrylic acid-alkyl copolymer, or a copolymer composed of an acrylic and methacrylic acid and a polyoxyethylene glycol ether of a higher alcohol in an amount of about 0.01 to 10% by weight;
   an alkali;
   water; and
   at least one of a surfactant, an oily agent, a hair dye, a moisturizer, a thickener, a preservative, an anti-oxidant, a UV absorber, a metal chelating agent, an enzyme, a pharmacologically active agent, or a perfume, wherein said composition is adjusted to a pH equal to or higher than $pK_1$ of uric acid with the alkali, wherein the uric acid is solubilized.

3. A method for stably solubilizing an aqueous cosmetic composition which consists essentially of from 0.01 to 2.0% by weight of uric acid, an acrylic polymer, wherein said acrylic polymer is a carboxyvinyl polymer mainly comprised of acrylic acid, an acrylic and methacrylic acid-alkyl copolymer, or a copolymer composed of an acrylic and methacrylic acid and a polyoxyethylene glycol ether of a higher alcohol in an amount of about 0.01 to 10% by weight, an alkali, water, and at least one of a surfactant, an oily agent, a hair dye, a moisturizer, a thickener, a preservative, an anti-oxidant, a UV absorber, a metal chelating agent, an enzyme, a pharmacologically active agent, or a perfume, which comprises adjusting pH of the composition to equal to or higher than $pK_1$ of uric acid with an alkali to solubilize uric acid.

4. The composition according to claim 2, wherein the composition is adjusted to pH 7.0 or higher.

5. The composition according to claim 2, wherein the alkali is an amine.

6. A method for stably solubilizing an aqueous cosmetic composition which consists essentially of from 0.01 to 2.0% by weight of uric acid, an acrylic polymer, wherein said acrylic polymer is a carboxyvinyl polymer mainly comprised of acrylic acid, an acrylic and methacrylic acid-alkyl copolymer, or a copolymer composed of an acrylic and methacrylic acid and a polyoxyethylene glycol ether of a higher alcohol in an amount of about 0.01 to 10% by weight, an alkali and water, which comprises adjusting pH of the composition to equal to or higher than $pK_1$ of uric acid with an alkali to solubilize uric acid.

7. The method according to claim 3, wherein the composition is adjusted to pH 7.0 or higher.

8. The method according to claim 3, wherein the alkali is an amine.

9. The composition according to claim 1, wherein the alkali is an amine.

10. The method according to claim 6, wherein the alkali is an amine.

11. The composition according to claim 2, wherein said uric acid is in an amount of from 0.1 to 1.3% by weight.

12. The method according to claim 3, wherein said uric acid is in an amount of from 0.1 to 1.3% by weight.

13. The composition according to claim 2, wherein said acrylic polymer is in an amount of from 0.1 to 5% by weight.

14. The method according to claim 3, wherein said acrylic polymer is in an amount of from 0.1 to 5% by weight.

15. The aqueous cosmetic composition according to claim 2, wherein said surfactant is cationic or nonionic, said oily agent is higher alcohol, higher fatty acid, paraffin wax, hydrocarbon oil, ester oil, or silicone oil, said hair dye is oxidation dye or direct dye, said moisturizer is glycerin or propylene glycol, and said enzyme is uricase.

16. The method according to claim 3, wherein said oily agent is higher alcohol, higher fatty acid, paraffin wax, hydrocarbon oil, ester oil, or silicone oil, said hair dye is oxidation dye or direct dye, said moisturizer is glycerin or propylene glycol, and said enzyme is uricase.

* * * * *